(12) United States Patent
Kobayashi

(10) Patent No.: US 9,452,496 B2
(45) Date of Patent: Sep. 27, 2016

(54) WELDING PORTION INSPECTION DEVICE AND INSPECTION METHOD THEREFOR

(71) Applicant: TOYOTA JIDOSHA KABUSHIKI KAISHA, Toyota-shi, Aichi-ken (JP)

(72) Inventor: Hiroomi Kobayashi, Okazaki (JP)

(73) Assignee: TOYOTA JIDOSHA KABUSHIKI KAISHA, Aichi-ken (JP)

( * ) Notice: Subject to any disclaimer, the term of this patent is extended or adjusted under 35 U.S.C. 154(b) by 0 days.

(21) Appl. No.: 14/781,112

(22) PCT Filed: Mar. 28, 2014

(86) PCT No.: PCT/IB2014/000446
§ 371 (c)(1),
(2) Date: Sep. 29, 2015

(87) PCT Pub. No.: WO2014/155188
PCT Pub. Date: Oct. 2, 2014

(65) Prior Publication Data
US 2016/0045985 A1     Feb. 18, 2016

(30) Foreign Application Priority Data

Mar. 29, 2013  (JP) ................. 2013-072090

(51) Int. Cl.
| | |
|---|---|
| G01N 21/00 | (2006.01) |
| B23K 31/12 | (2006.01) |
| B23K 26/03 | (2006.01) |
| G01N 21/55 | (2014.01) |
| G01N 21/88 | (2006.01) |

(52) U.S. Cl.
CPC ........... *B23K 31/125* (2013.01); *B23K 26/032* (2013.01); *B23K 26/21* (2015.10); *G01N 21/55* (2013.01); *G01N 21/88* (2013.01); *G01N 2201/12* (2013.01)

(58) Field of Classification Search
CPC ............ B23K 1/0056; B23K 2201/34; B23K 2203/02; B23K 2203/50; B23K 26/032; B23K 26/1429; B23K 26/20; B23K 26/32; B23K 26/3206; B23K 26/322; B23K 26/3293; B23K 26/34; B23K 28/02; G05B 13/0265
See application file for complete search history.

(56) References Cited

U.S. PATENT DOCUMENTS

| | | |
|---|---|---|
| 2005/0163364 A1 | 7/2005 | Beck et al. |
| 2009/0159579 A1 | 6/2009 | Nishio et al. |

FOREIGN PATENT DOCUMENTS

| | | |
|---|---|---|
| CN | 1709631 A | 12/2005 |
| CN | 101287572 A | 10/2008 |
| EP | 2 543 464 A2 | 1/2013 |

(Continued)

*Primary Examiner* — Michael P Stafira
(74) *Attorney, Agent, or Firm* — Sughrue Mion, PLLC

(57) ABSTRACT

Welding laser beam is irradiated along welding trajectories set in works, or inspection laser beam is irradiated along scanning trajectories set in a molten pool in the works which has been melted by the welding laser beam. Return light including reflected light from the molten pool in the work, evaporation luminescence generated by melting/evaporating of the work and thermal radiation light radiated from the molten pool in the work is received. A fundamental frequency is detected by conducting Fourier transform on the intensity of the received return light and a welding condition of the welding portion in the work is inspected based on an amplitude under the fundamental frequency and an amplitude under a frequency that is twice as high as the fundamental frequency.

6 Claims, 14 Drawing Sheets

(56) References Cited

FOREIGN PATENT DOCUMENTS

| | | |
|---|---|---|
| JP | 2001-352145 A | 12/2001 |
| JP | 2003-220483 A | 8/2003 |
| JP | 2005-230913 A | 9/2005 |
| JP | 2007-105775 A | 4/2007 |
| JP | 2007-283392 A | 11/2007 |
| JP | 2008-087056 A | 4/2008 |
| JP | 2014-195822 A | 10/2014 |
| JP | 2014-198345 A | 10/2014 |
| WO | 2014/155190 A2 | 10/2014 |
| WO | 2014/155191 A2 | 10/2014 |

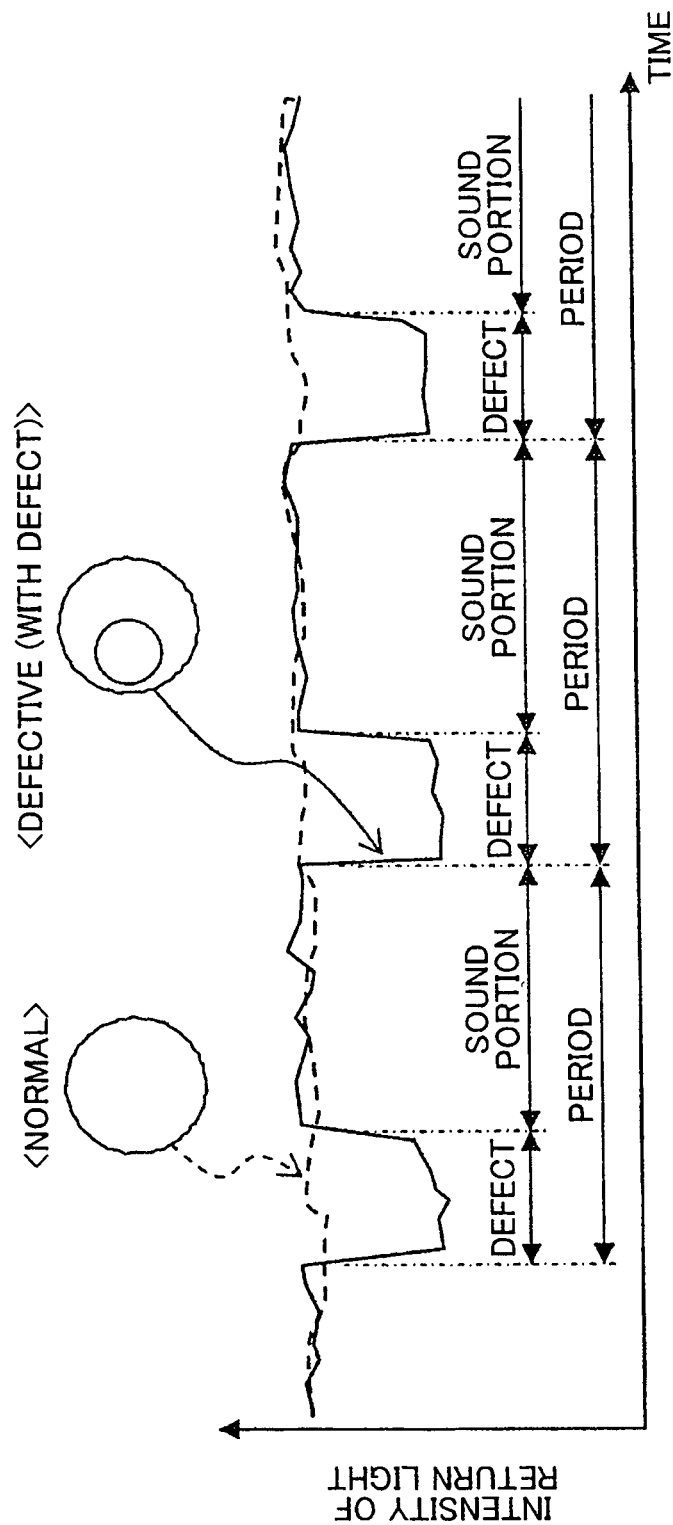

WELDING PORTION INSPECTION DEVICE AND INSPECTION METHOD THEREFOR

BACKGROUND OF THE INVENTION

1. Field of the Invention

The present invention relates to a welding portion inspection device and an inspection method therefor, particularly to an inspection device which inspects a welding condition of a welding portion formed when a plurality of works are welded together by means of laser beam and an inspection method therefor, for example.

2. Description of Related Art

When two steel sheets are welded together by means of laser beam such that they are stacked one upon another, the quality evaluation of a welding portion formed by laser welding has been performed. As an example of the quality evaluation on the welding portion formed by laser welding, for example, Japanese Patent Application Publication No. 2008-87056 (JP 2008-87056 A) has disclosed a technology concerning the quality evaluation on the laser welding using reflected light of the laser beam.

A laser welding quality determination system disclosed in JP 2008-87056 A radiates. YAG laser, for example, from a laser torch. A laser reflected light is received by a first reflected light receiving/outputting device from a forward-diagonally upward side in the advance direction of welding operation. A welding light including evaporative light (plume) and reflected laser light is received by a second reflected light receiving/outputting device coaxially with the radiation direction of laser beam. The laser reflected light and welding light received from two predetermined directions at the same time are converted to an electric signal corresponding to their intensities. This system determines the welding quality based on the signal intensity of this electric signal and changes in the intensity thereof.

According to the laser welding quality determination system disclosed in JP 2008-87056 A, the reflected laser light and the welding light are received from two different directions at the same time. By comparing the signal intensity of each of received lights with a threshold set appropriately, it is possible to determine that any one of various welding defects such as underfill in which welding bead sinks to fill a gap between steel sheets, joint failure in which upper and lower steel sheets fail to joint due to an excessive gap between the steel sheets, bead depression in which bead is depressed due to an excessive gap between steel sheets, fusing in which bead vanishes abruptly due to a change in heat balance, boring has occurred.

However, according to the laser welding quality determination system disclosed in JP 2008-87056 A, for example, if a laser torch and a work (steel sheet) are set apart from each other, the electric signal obtained from the received reflected laser beam or welding light may be very weak. Thus, the accuracy for determination of welding failure may drop. Particularly, in the case of bead depression in which bead is depressed upon laser welding, the change in electric signal due to welding failure decreases. Thus, sometimes, welding failure in a work cannot be detected precisely. Further it has been known that evaporation luminescence generated due to melting/evaporating of a work or heat radiation light radiated from a molten pool in the work changes depending on a work temperature and that a threshold for determining the electric signal obtained from the received reflected laser beam or welding light and the laser welding quality changes depending on the work temperature. If the change in the work temperature upon laser welding is large, the determination accuracy for the work welding defect sometimes may further drop.

SUMMARY OF THE INVENTION

The present invention provides a welding portion inspection device capable of inspecting a welding condition of a welding portion in a work precisely in a remote welding operation for welding with a laser torch and the work set apart from each other, for example, and an inspection method therefor.

A first aspect of the present invention relates to a welding portion inspection device configured to inspect a welding condition of a welding portion formed when a plurality of works is welded together. The welding portion inspection device includes: an irradiation portion configured to irradiate welding laser beam along a welding trajectory set in works or irradiate inspection laser beam along a scanning trajectory set in a molten pool of the work melted by the welding laser beam so as to weld together the works; a light receiving portion configured to receive return light including at least one of reflected light from the molten pool in the work by the welding laser beam or the inspection laser beam irradiated by the irradiation portion, evaporation luminescence which is generated by evaporating of the work, and thermal radiation light radiated from the molten pool in the work; and an inspecting portion configured to inspect the welding condition of the welding portion in the work based on an amplitude under a fundamental frequency which is detected by conducting Fourier transform on the intensity of the return light received by the light receiving portion and another amplitude under a frequency that is twice as high as the fundamental frequency.

According to the above-described aspect, the welding condition of the welding portion in the work is inspected based on an amplitude under the fundamental frequency detected by conducting Fourier transform on the intensity of return light received by a light receiving portion when irradiating welding laser beam along a welding trajectory or irradiating inspection laser beam along a scanning trajectory and another amplitude under a frequency that is twice as high as the fundamental frequency. As a result, in a remote welding operation for welding together works with the irradiation portion and those works set apart from each other, even if electric signal obtained from the return light received by the light receiving portion is weak or the intensity of the return light received by the light receiving portion changes corresponding to changes in the temperature of the works, the welding condition of the welding portion in the work can be inspected precisely.

In the above-described aspect, the inspecting portion may inspect the size of a welding defect in the welding portion of the work based on a ratio between the amplitude under the fundamental frequency and the amplitude under another frequency that is twice as high as the fundamental frequency.

According to the above-described aspect, the inspecting portion inspects the size of the welding defect in the welding portion of the work based on a ratio between an amplitude under the fundamental frequency and another amplitude under the frequency that is twice as high as the fundamental frequency thereby making it possible to inspect the welding condition of the welding portion in the work more precisely.

In the above-described aspect, the irradiation portion may irradiate the welding laser beam along an identical welding trajectory several times or may irradiate the inspection laser beam along an identical scanning trajectory several times.

According to the above-described aspect, the welding condition of the welding portion in the work is inspected based on an amplitude under the fundamental frequency detected by conducting Fourier transform on the intensity of the return light received by the light receiving portion when irradiating the welding laser beam along an identical welding trajectory several times or irradiating the inspection laser beam along an identical scanning trajectory several times and an amplitude under another frequency that is twice as high as the fundamental frequency. As a result, even if electric signal obtained from the return light when irradiating the welding laser beam along a predetermined welding trajectory only once or irradiating the inspection laser beam along a predetermined scanning trajectory only once is weak or the electric signal obtained from the return light contains noise, reduction in inspection accuracy due to such a noise contained in the return light can be suppressed That is, the inspection accuracy for the welding condition of the welding portion can be increased.

A second aspect of the present invention relates to a welding portion inspection method adapted to inspect a welding condition of a welding portion formed when a plurality of works is welded together. The welding portion inspection method includes irradiating the welding laser beam along the welding trajectory set in the works or irradiating the inspection laser beam along the scanning trajectory set in the molten pool of the works melted by the welding laser beam so as to weld together the works; receiving return light including at least one of reflected light from the molten pool in the works by the welding laser beam or the inspection laser beam, evaporation luminescence which is generated by evaporating of the work, and thermal radiation light radiated from the molten pool in the work; detecting a fundamental frequency by conducting Fourier transform on the intensity of the return light; and inspecting the welding condition of the welding portion in the work based on an amplitude under the fundamental frequency and another amplitude under another frequency that is twice as high as the fundamental frequency.

According to the above-described aspect, the fundamental frequency is detected by conducting Fourier transform on the intensity of the received return light and then, the welding condition of the welding portion in the work is inspected based on the amplitude under the fundamental frequency and the amplitude under another frequency that is twice as high as the fundamental frequency. As a result, in a remote welding operation for welding together with the laser irradiation portion and the works set apart from each other, even if electric signal obtained from the received return light is weak or the intensity of the received return light changes corresponding to changes in the temperature of the works, the welding condition of the welding portion in the work can be inspected precisely.

As understood from the above description, according to the first and second aspects of the present invention, upon welding together a plurality of works, the fundamental frequency is detected by conducting Fourier transform on the intensity of the return light when irradiating the welding laser beam along the welding trajectory or irradiating the inspection laser beam along the scanning trajectory and then, the welding condition of the welding portion in the work is inspected based on the amplitude under the fundamental frequency and the amplitude under another frequency that is twice as high as the fundamental frequency. As a result, even if the electric signal obtained from the return light is weak or the intensity of the return light changes corresponding to changes in the work temperature, the welding condition of the welding portion in the work can be inspected precisely.

BRIEF DESCRIPTION OF THE DRAWINGS

Features, advantages, and technical and industrial significance of exemplary embodiments of the invention will be described below with reference to the accompanying drawings, in which like numerals denote like elements, and wherein:

FIG. 4 is a diagram showing an example of the intensity of return light in time series;

DETAILED DESCRIPTION OF EMBODIMENTS

As a result of energetic researches, the inventors of the present invention have found out that an amplitude of return light under a fundamental frequency detected by conducting Fourier transform to the intensity of the return light received when welding laser beam or inspection laser beam is irradiated on a work and another amplitude thereof under a frequency that is twice as high as the fundamental frequency are closely related to a welding condition of a welding portion formed on the work, more specifically the size of a welding defect in the welding portion.

More specifically, from a result obtained by conducting Fourier transform on the intensity of various return lights when a welding defect exists in the welding portion of work, it has been found out that a ratio between the amplitude of the return light under the fundamental frequency and the amplitude thereof under another frequency that is twice as high as the fundamental frequency is correlated to the size of the welding defect in the welding portion of a work.

Hereinafter, embodiments of the welding portion inspection device and inspection method therefor according to the present invention will be described with reference to the accompanying drawings.

[First Embodiment of a Welding Portion Inspection Device]

Figure 2:
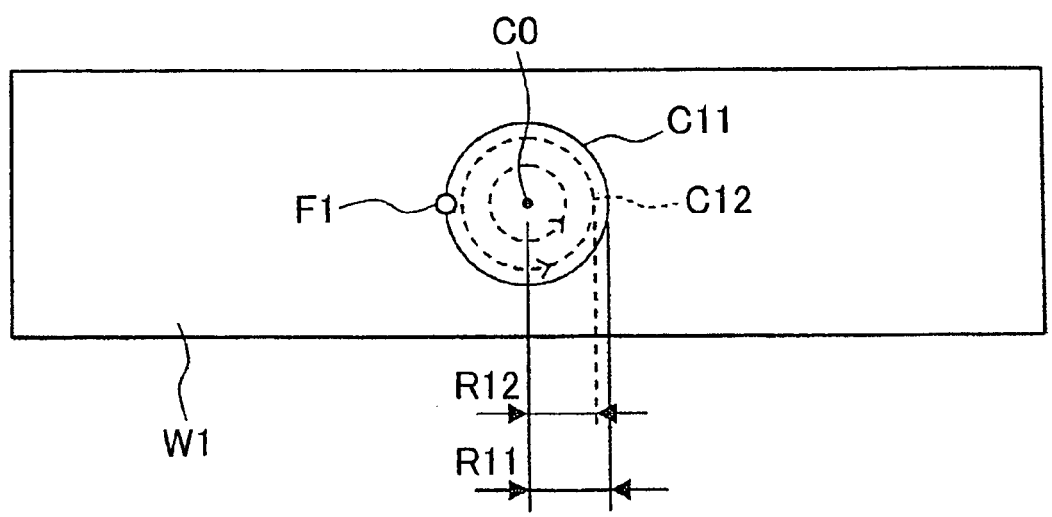
FIG. 2 is a top view describing a radiation state of welding laser beam by means of a welding radiation portion of the inspection device shown in FIG. 1.
Figure 3:
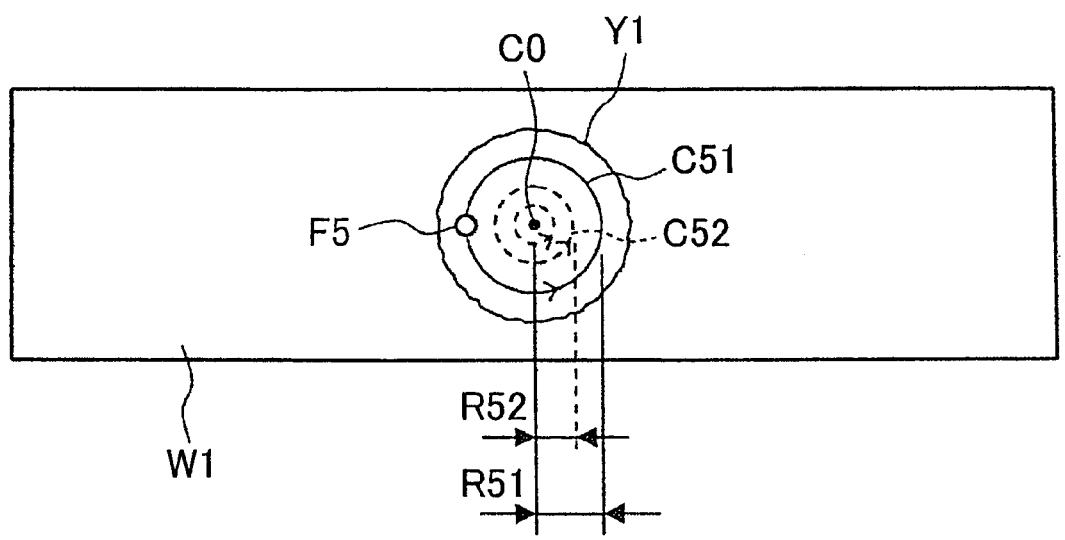
FIG. 3 is a top view describing a radiation state of inspection laser beam by means of an inspection radiation portion of the inspection device shown in FIG. 1.

First, the first embodiment of the welding portion inspection device of the present invention will be described with reference to FIGS. 1 to 3.

Figure 1:
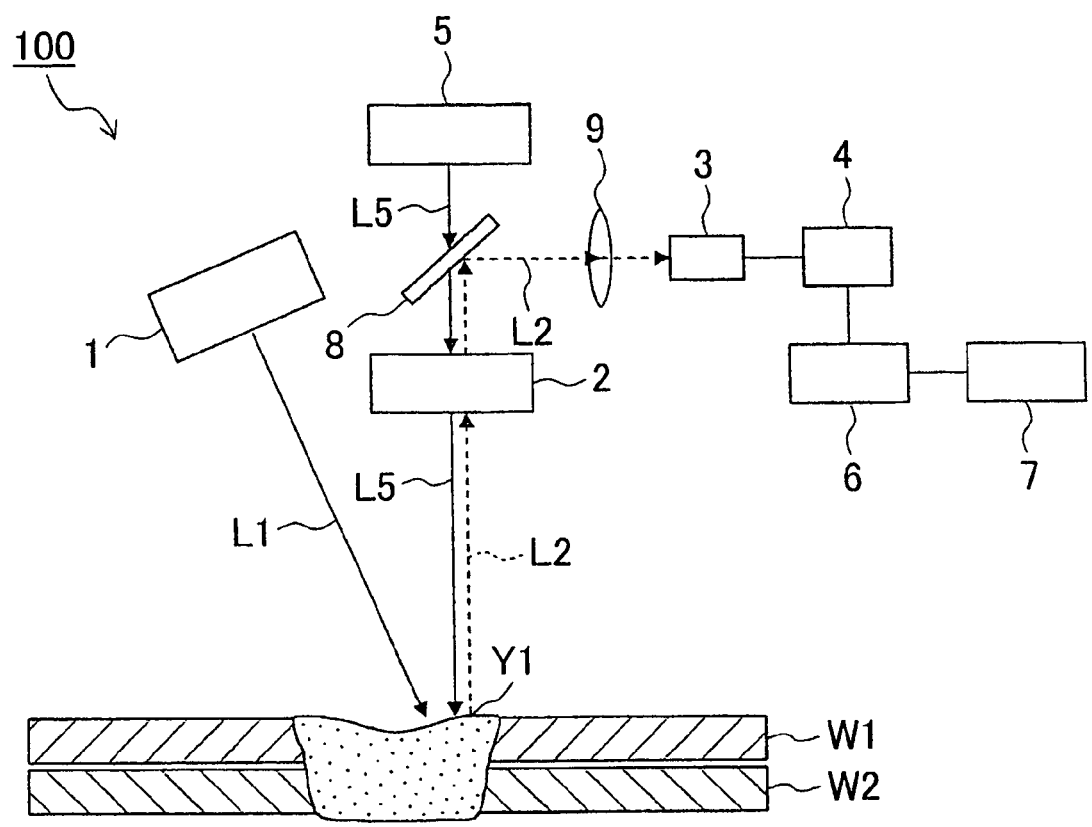
FIG. 1 is an overall configuration diagram showing an entire structure of a first embodiment of a welding portion inspection device of the present invention.

FIG. 1 is an overall configuration diagram showing an entire structure of the first embodiment of a welding portion inspection device of the present invention. FIG. 2 is a top view describing a radiation state of welding laser beam by means of a welding radiation portion of the inspection device shown in FIG. 1, and FIG. 3 is a top view describing a radiation state of inspection laser beam by means of an inspection radiation portion of the inspection device shown in FIG. 1.

The inspection device 100 shown in FIG. 1 includes mainly a welding irradiation portion 1, an inspection irradiation portion 5, a light receiving portion 2, a converting portion 3, an amplifier 4, an inspecting portion 6, and an cathode ray tube (CRT) 7.

The welding irradiation portion 1 irradiates two works W1, W2 with welding laser beam (e.g., YAG laser having a predetermined laser wavelength) L1 to weld together the two works W1, W2 (e.g., steel sheet) stacked one upon another or disposed slightly apart from each other. More specifically, as shown in FIG. 2, the welding irradiation portion 1 turns a focus F1 of welding laser beam L1 along a substantially circular welding trajectory C11 having a radius R11 set on the work W1 several times and irradiates over the welding trajectory C11 with the welding laser beam L1 several times. Next, the focus F1 of the welding laser beam L1 is moved inside the welding trajectory C11. Subsequently, the focus F1 of the welding laser beam L1 is turned along a substantially circular welding trajectory C12 which has a smaller radius R12 than the radius R11 and is coaxial with the welding trajectory C11 several times and irradiates the welding laser beam L1 over the welding trajectory C12 several times. By repeating the irradiation step of the welding laser beam L1 in this way, the substantially circular welding portion is formed on the works W1, W2 so as to weld together the works W1, W2 (called laser screw welding). In the meantime, a center C0 of the welding trajectory C11 and the welding trajectory C12 serves as a welding center of the welding portions to be formed on the works W1, W2.

By irradiation of the welding laser beam L1 by means of the welding irradiation portion 1, molten pool Y1 is formed as a result of melting of the works W1, W2 on the right and left of the welding laser beam L1 and in the back thereof with respect to an advance direction of the welding laser beam L1. In the first embodiment, the welding laser beam L1 is irradiated along the substantially circular welding trajectories C1, C2 as described above. As a result, the substantially circular molten pool Y1 is formed in the works W1, W2.

As shown in FIG. 1, the inspection irradiation portion 5 irradiates inspection laser beam L5 to the molten pool Y1 in a molten state through an optical system 8 and a light receiving portion 2. More specifically, as shown in FIG. 3, the inspection irradiation portion 5 turns the focus F5 of the inspection laser beam L5 along a substantially circular scanning trajectory C51 having a radius R51 set inside an outer edge of the molten pool Y1 at a substantially constant speed several times and irradiates the inspection laser beam L5 over the scanning trajectory C51 several times. Next, the focus F5 of the inspection laser beam L5 is moved inside the scanning trajectory C51. Subsequently, the focus F5 of the inspection laser beam L5 is turned along a substantially circular scanning trajectory C52 which has a smaller radius R52 than the radius R51 and is coaxial with the scanning trajectory C51 several times and the inspection laser beam L5 is irradiated over the scanning trajectory C52 several times. By repeating the irradiation step of the inspection laser beam L5, the inspection irradiation portion 5 irradiates the inspection laser beam L5 over the substantially circular entire molten pool Y1 formed in the works W1, W2. In the meantime, the center of the scanning trajectories C51, C52 is set to the center C0 of the aforementioned welding trajectories C11, C12.

As shown in FIG. 1, with the inspection irradiation portion 5 irradiating the inspection laser beam L5 to the molten pool Y1, the light receiving portion 2 receives return light L2 including reflected light from the molten pool Y1 of the works W1, W2 by the inspection laser beam L5, evaporation luminescence which is generated by melting/evaporating of the works W1, W2 (plasma light), and thermal radiation light (infrared light) radiated from the molten pool Y1 of the works W1, W2.

The converting portion 3 converts the return light L2 which has been received by the light receiving portion 2 and condensed through the optical system 8 and the condensing lens 9 to electric signal and outputs the electric signal to the amplifier 4. The amplifier 4 amplifies the signal intensity of the electric signal output from the converting portion 3 and sends to the inspecting portion 6.

The inspecting portion 6 processes the electric signal which has been transmitted from the amplifier 4 to inspect a welding condition of a welding portion formed on the works W1, W2. More specifically, the inspecting portion 6 conducts Fourier transform on the intensity of the return light L2 which has been received by the light receiving portion 2 when the inspection irradiation portion 5 irradiates the inspection laser beam L5 to the molten pool Y1 along the respective scanning trajectories C51, C52 several times. Next, it detects a fundamental frequency in which its amplitude peak is first detected from a relationship between the frequency and amplitude after the Fourier transform. The size of a welding defect in the welding portion formed in the works W1, W2 is inspected based on a ratio between the amplitude of the fundamental frequency and the amplitude of a frequency that is twice as high as the fundamental frequency. The inspecting portion 6 sends a signal processing result of the electric signal sent from the amplifier 4 to the CRT 7. The CRT 7 displays the signal processing result sent from the inspecting portion 6.

[First Embodiment of Welding Portion Inspection Method]

Next, the first embodiment of the welding portion inspection method of the present invention using the inspection device 100 of the welding portion shown in FIG. 1 will be described with reference to FIGS. 4 to 7.

Figure 5A:
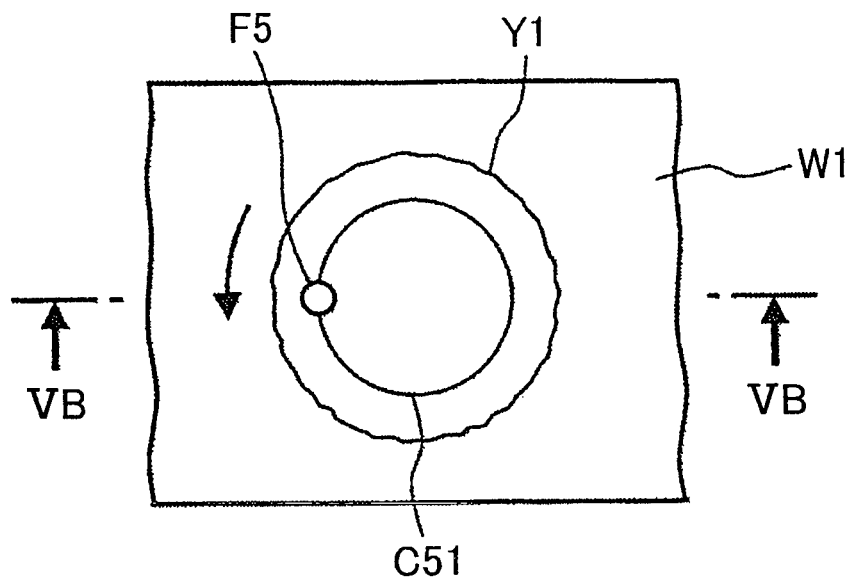
FIG. 5A is a top view describing a relationship between a molten pool and a scanning trajectory of inspection laser beam when the welding condition of a welding portion is normal.
Figure 5B:
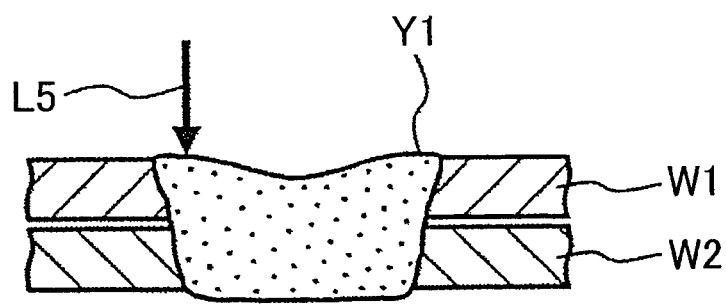
FIG. 5B is a view taken along the line VB-VB in FIG. 5A.
Figure 6A:
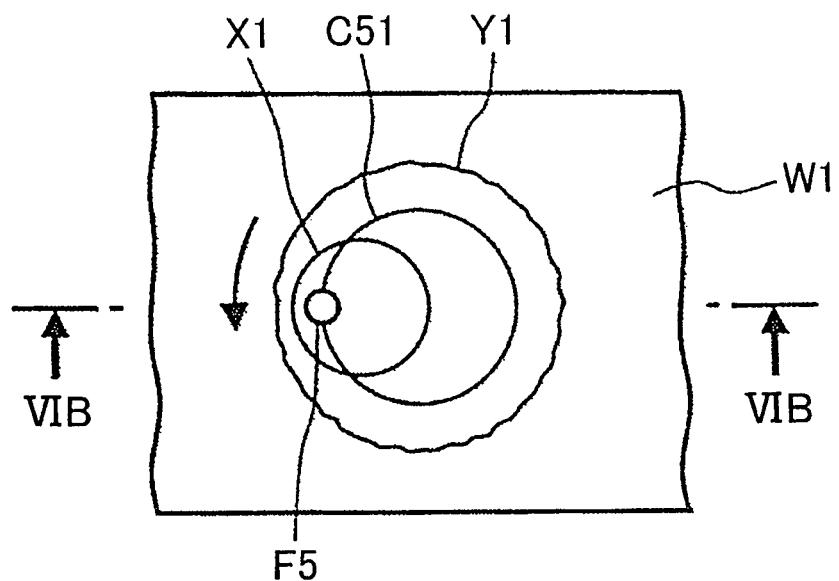
FIG. 6A is a top view describing a relationship between the molten pool and the scanning trajectory of inspection laser beam when the welding condition of the welding portion is defective.
Figure 6B:
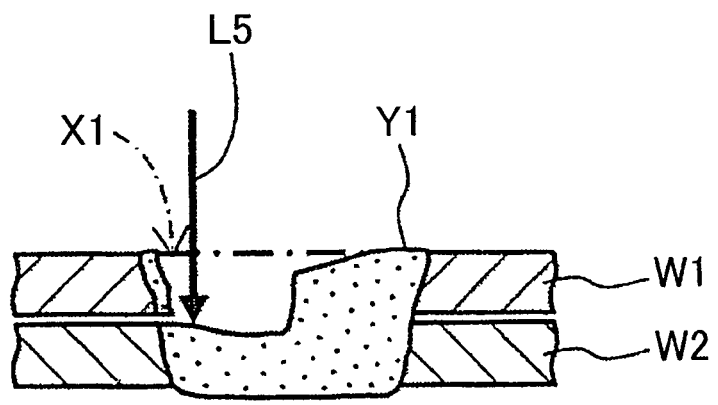
FIG. 6B is a view taken along the line VIB-VIB in FIG. 6A.
Figure 7:
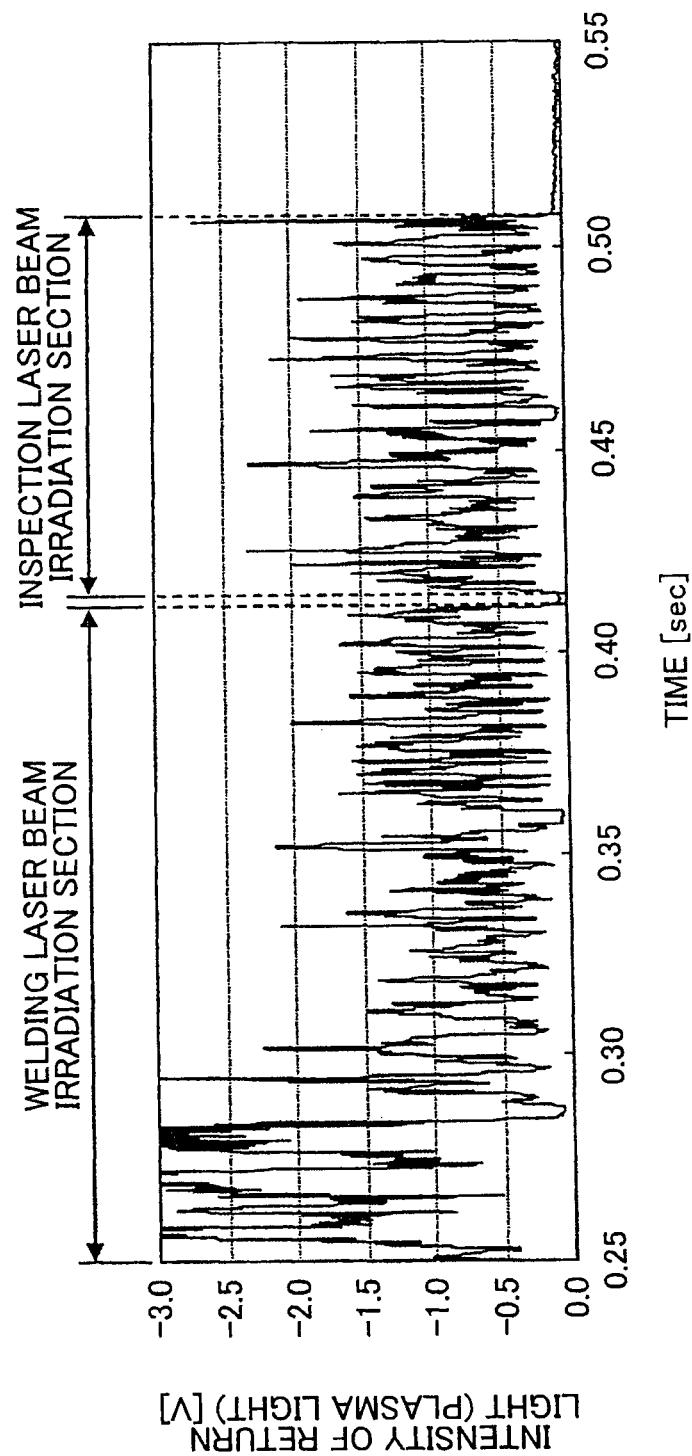
FIG. 7 is a diagram showing the intensity of return light to be measured actually in time series.

FIG. 4 is a diagram showing an example of the intensity of return light in time series which is to be sent to the inspecting portion 6 of the inspection device 100 shown in FIG. 1. FIG. 5A is a top view describing a relationship between a molten pool in case where the welding condition of a welding portion is normal and the scanning trajectory of inspection laser beam. FIG. 5B is a view taken along the line VB-VB in FIG. 5A. FIG. 6A is a top view describing a relationship between the molten pool and the scanning trajectory of inspection laser beam when the welding condition of the welding portion is defective. FIG. 6B is a view taken along the line VIB-VIB in FIG. 6A. FIG. 7 is a diagram showing the intensity of return light to be measured actually, particularly the intensity of evaporation luminescence (plasma light) which is generated by melting/evaporating of the works W1, W2, in time series.

If, when a welding condition of a welding portion is normal as shown in FIG. 5A and FIG. 5B (when the works W1, W2 are normally welded together), the focus F5 of the inspection laser beam L5 is turned along the substantially circular scanning trajectory C51 set in the molten pool Y1, for example, several times to irradiate the inspection laser beam L5 over the scanning trajectory C51 several times, it is considered that the change in intensities of the reflected light, evaporation luminescence and heat radiation by the inspection laser beam L5 from the works W1, W2 is relatively small. Thus, as shown with a dotted line in FIG. 4, the change in intensity of the return light L2 which is sent to the inspecting portion 6 through the converting portion 3 and the amplifier 4 after received by the light receiving portion 2 is relatively small.

On the other hand, if, when the welding condition of the welding portion is defective as shown in FIG. 6A and FIG. 6B (for example, in the case of one side work depressed welding which is caused when welding bead on one of works is depressed), the focus F5 of the inspection laser beam L5 is turned along the substantially circular scanning trajectory C51 set in the molten pool Y1, for example, several times to irradiate the inspection laser beam L5 over the scanning trajectory C51 several times, and if any welding defect X1 (a part in which molten metal is missing) exists on the scanning trajectory C51 of the inspection laser beam L5, the intensity of reflected light of the inspection laser beam L5 from the works W1, W2 decreases at a point where the welding defect X1 exists of the scanning trajectory C51. As a result, as shown with a solid line in FIG. 4, the intensity of the return light L2 which is sent to the inspecting portion 6 through the converting portion 3 and the amplifier 4 after received by the light receiving portion 2 decreases periodically at a point where the welding defect X1 exists within a scanning period (for example, a period in which the inspection laser beam L5 makes a single turn along the scanning trajectory C51) of the inspection laser beam L5.

That is, a ratio between a length passing the welding defect X1 of the scanning trajectory and a length passing a sound portion other than the welding defect X1 coincides with a ratio between a time when the inspection laser beam L5 swept at a substantially constant speed passes the welding defect X1 in the scanning trajectory and a time when it passes the sound portion other than the welding defect X1. Thus, according to the inspection method of the first embodiment, the periodicity of the change in the intensity of the return light L2 is analyzed by the inspecting portion 6. More specifically, when the inspection laser beam L5 is irradiated along the respective scanning trajectories C51, C52 several times, Fourier transform is conducted on the intensity of the return light L2 which is received by the light receiving portion 2. Then, the fundamental frequency whose amplitude peak first is detected from a relationship between the frequency and the amplitude after Fourier transform is detected. A ratio between the amplitude of the fundamental frequency and the amplitude of a frequency that is twice as high as the fundamental frequency is calculated. As a result, even if electric signal obtained from the return light L2 is weak or the intensity of the return light L2 changes corresponding to a change in the temperature of the work, the size of the welding defect X1 which can exist inside the outer edge of the molten pool Y1 can be inspected. Particularly, according to the first embodiment, the inspection laser beam L5 is irradiated along the substantially circular scanning trajectory with respect to the molten pool Y1. Thus, the size of a welding defect X1 which can exist inside the outer edge of the welding pool Y1 eccentrically from the welding center C0 or the size of a welding defect X1 of a non-circular shape such as an elliptical shape and a substantially polygon shape can be inspected.

Further, according to the first embodiment, the inspection laser beam L5 is irradiated along the scanning trajectories C51, C52 set in the molten pool Y1 formed by irradiating with the welding laser beam L1. Based on the periodicity of a change in the intensity of the return light L2 which is received by the light receiving portion 2 when the inspection laser beam L5 is irradiated along the scanning trajectories C51, C52, a welding condition of a welding portion is inspected. As a result, even if irradiation condition of the welding laser beam L1 changes or the focus point of the welding laser beam deflects from a generation position of the welding defect X1, the scanning condition (scanning trajectory or scanning speed) of the inspection laser beam L5 can be adjusted appropriately. Thus, the welding condition of the welding portion formed on a work can be inspected precisely.

According to an example shown with a solid line in FIG. 4, in the intensity of the return light L2 received by the light receiving portion 2, the size of the welding defect X1 can be estimated by estimating a length passing the welding defect X1 of the scanning trajectory and a length passing a sound portion other than the welding defect X1 from a time when the inspection laser beam L5 passes the welding defect X1 in the scanning trajectory and a time when it passes a sound portion other than the welding defect X1. However, the intensity of the return light L2 which is actually received by the light receiving portion 2 contains intensity signals with various frequencies, as shown in FIG. 7. Thus, it is necessary to inspect the size of the welding defect X1 from a relationship between the frequency and the amplitude obtained by conducting Fourier transform on the intensity of the return light L2 received by the light receiving portion 2.

[Second Embodiment of Welding Portion Inspection Device]

Next, the second embodiment of the welding portion inspection device of the present invention will be described with reference to FIG. 8.

Figure 8:
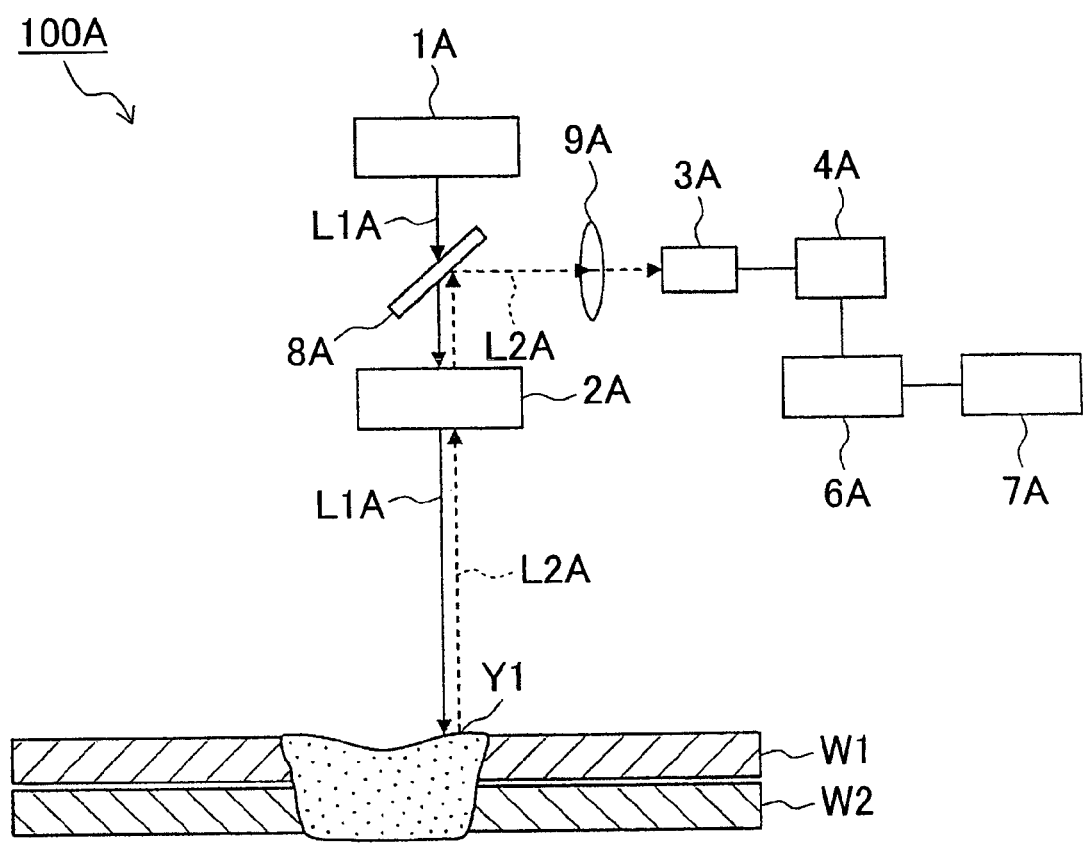
FIG. 8 is an overall configuration diagram showing the entire structure of a second embodiment of the welding portion inspection device of the present invention.

FIG. 8 is an overall configuration diagram showing the entire structure of the second embodiment of the welding portion inspection device of the present invention. The inspection device 100A of the second embodiment shown in FIG. 8 is different from the inspection device 100 of the first embodiment shown in FIG. 1 in inspecting the welding condition of the welding portion using reflected light of the welding laser beam irradiated from the welding irradiation portion. Other structure is almost the same as the inspection device 100 of the first embodiment. Therefore, a detailed description of the same structure as the first embodiment is omitted while like reference numerals are attached to like components.

The inspection device 100A shown in the Figure includes mainly a welding irradiation portion 1A, a light receiving portion 2A, a converting portion 3A, an amplifier 4A, an inspecting portion 6A, and a CRT 7A.

The welding irradiation portion 1A irradiates two works W1, W2 with welding laser beam L1 through an optical system 8A and the light receiving portion 2A to weld together the two works W1, W2 stacked one upon another or disposed slightly apart from each other. By irradiation of the welding laser beam L1A by means of the welding irradiation portion 1A, molten pool Y1 is formed as a result of melting of the works W1, W2 on the right and left of the welding laser beam L1A and in the back thereof with respect to an advance direction of the welding laser beam L1A.

The light receiving portion 2A receives return light L2A including reflected light from the molten pool Y1 of the works W1, W2 by the welding laser beam L1A which is irradiated from the welding irradiation portion 1A, evaporation luminescence which is generated by melting/evaporating of the works W1, W2 (plasma light), and thermal radiation light (infrared light) radiated from the molten pool Y1 of the works W1, W2.

The converting portion 3A converts the return light L2A which has been received by the light receiving portion 2A and condensed through the optical system 8A and the condensing lens 9A to electric signal and outputs the electric signal to the amplifier 4A. The amplifier 4A amplifies the signal intensity of the electric signal output from the converting portion 3A and sends to the inspecting portion 6A.

The inspecting portion 6A processes the electric signal which has been transmitted from the amplifier 4A to inspect the welding condition of the welding portion formed on the works W1, W2. More specifically, the inspecting portion 6A conducts Fourier transform on the intensity of the return light L2A which has been received by the light receiving portion 2A when the welding irradiation portion 1A irradiates the welding laser beam L1A along the scanning trajectory. Next, it detects a fundamental frequency whose amplitude peak is first detected from a relationship between the frequency and amplitude after the Fourier transform. The size of a welding defect in the welding portion formed in the works W1, W2 is inspected based on a ratio between the amplitude of the fundamental frequency and the amplitude of a frequency that is twice as high as the fundamental frequency. The inspecting portion 6A sends a signal processing result of the electric signal sent from the amplifier 4A to the CRT 7A. The CRT 7A displays the signal processing result sent from the inspecting portion 6A.

The change in the intensity of the return light L2A which is received by the light receiving portion 2A when the welding laser beam L1A is irradiated along the welding trajectory is relatively small in case in which the welding condition of the welding portion is normal, like the first embodiment. On the other hand, in case in which the welding condition of the welding portion is defective, if the welding defect (a portion in which any molten metal is missing) is formed on the welding trajectory of the welding laser beam L1A, the intensity of the return light L2A which is received by the light receiving portion 2A when the welding laser beam L1A is irradiated along the welding trajectory decreases periodically at the position where the welding defect is formed.

According to the second embodiment, the periodicity of the change in the intensity of the return light L2A is analyzed by the inspecting portion 6A. More specifically, when the welding laser beam L1A is irradiated along the welding trajectory, Fourier transform is conducted on the intensity of the return light L2A which is received by the light receiving portion 2A. Then, the fundamental frequency whose amplitude peak first is detected from a relationship between the frequency and the amplitude after Fourier transform is detected. A ratio between the amplitude of the fundamental frequency and the amplitude of a frequency that is twice as high as the fundamental frequency is calculated. As a result, even if electric signal obtained from the return light L2A is weak or the intensity of the return light L2A changes corresponding to a change in the temperature of the work, the size of the welding defect which can exist inside the outer edge of the molten pool Y1 can be inspected.

In the meantime, in the above-described first embodiment, an embodiment in which the center of the scanning trajectory of the inspection laser beam is set on the center of the welding trajectory of the welding laser beam has been described. However, the center of the scanning trajectory of the inspection laser beam may be set at an appropriate position inside the molten pool formed by irradiation of the welding laser beam.

In the above-described embodiment, an embodiment in which the welding trajectory of the welding laser beam and the scanning trajectory of the inspection laser beam are substantially circular has been described. However, the welding trajectory of the welding laser beam and the scanning trajectory of the inspection laser beam may be in a closed loop shape such as an elliptical shape, polygon shape or in a curve or straight line of a predetermined length. If a position where the welding defect in the welding portion is likely to occur can be estimated, preferably, the welding trajectory of the welding laser beam or the scanning trajectory of the inspection laser beam is set so as to pass that position. In the meantime, if the welding trajectory of the welding laser beam is in a closed loop shape such as the elliptical shape, polygon shape, the center of the welding can be set on the gravity center of the welding trajectory.

In the above-described embodiment, an embodiment in which welding laser beam or inspection laser beam is irradiated to a work fixed at a predetermined position has been described. However, it is permissible to weld works together with laser beam by moving the works appropriately with the focuses of the welding laser beam and the inspection laser beam fixed. Alternatively, it is also permissible to weld works together by moving both the works and the focus of the welding laser beam or the inspection laser beam relatively to each other.

[Analysis and Results of Estimating a Relationship Between the Intensity of Return Light and the Size of Welding Defect in a Welding Portion Using an Analytical Model]

The inventors of the present invention made four kinds of analytical models each having a welding defect of a different size (examples 1-4) and evaluated a relationship between the intensity of the return light based on each analytical model and the size of the welding defect in each welding portion.

<Shape of Analytical Model and Intensity of Return Light Therein>

First, the shape of the analytical model will be described with reference to FIGS. 9A, 10A, 11A and 12A. It was assumed that the ratio of the length passing the welding defect with respect to the length passing the sound portion of the substantially circular scanning trajectory of the inspection laser beam was 1.00 in the example 1 shown in FIG. 9A, 0.67 in the example 2 shown in FIG. 10A, 0.33 in the example 3 shown in FIG. 11A and 0.11 in the example 4 shown in FIG. 12A. That is, it was found that the ratio of the length passing the welding defect with respect to the overall scanning trajectory of the inspection laser beam was ½ (50%) in the example 1 shown in FIG. 9A, ⅖ (40%) in the example 2 shown in FIG. 10A, ¼ (25%) in the example 3 shown in FIG. 11A and ¹⁄₁₀ (10%) in the example 4 shown in FIG. 12A.

Figure 9A:
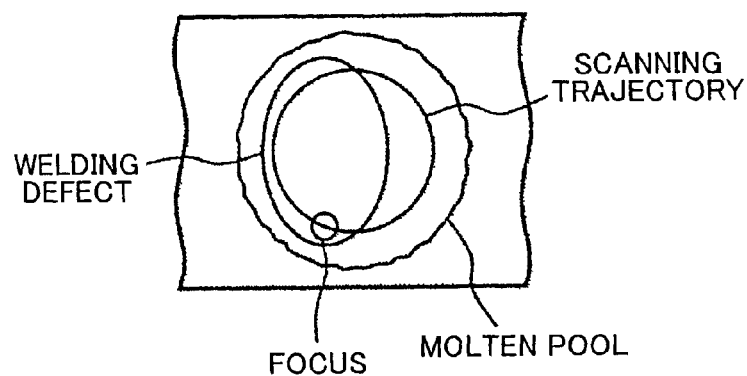
FIG. 9A is an enlarged top view showing the welding portion according to the example 1 based on analytical model.
Figure 9B:
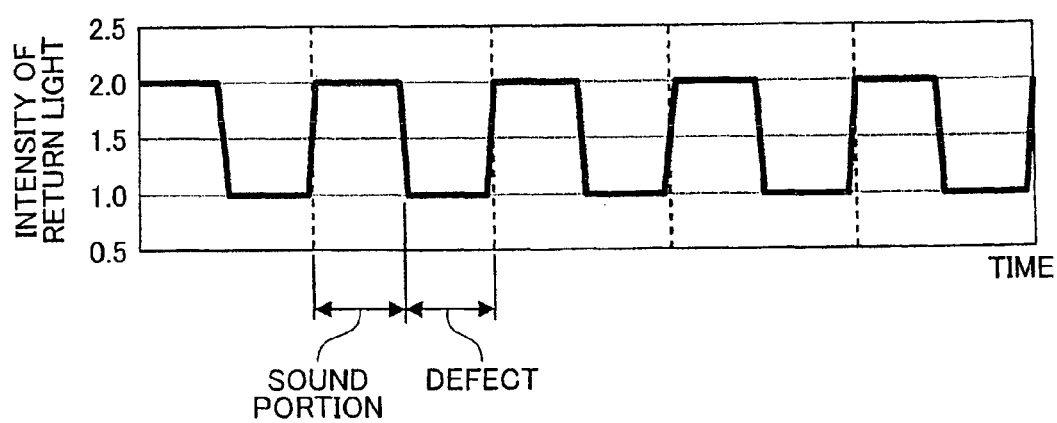
FIG. 9B is a diagram showing the intensity of return light according to the example 1 estimated from the analytical model in time series.
Figure 10A:
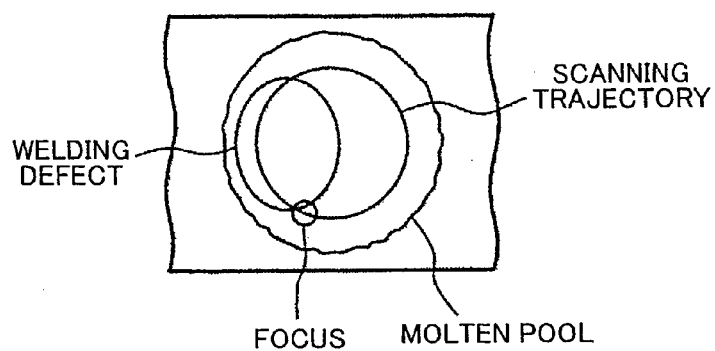
FIG. 10A is an enlarged top view showing the welding portion according to the example 2 based on analytical model.
Figure 10B:
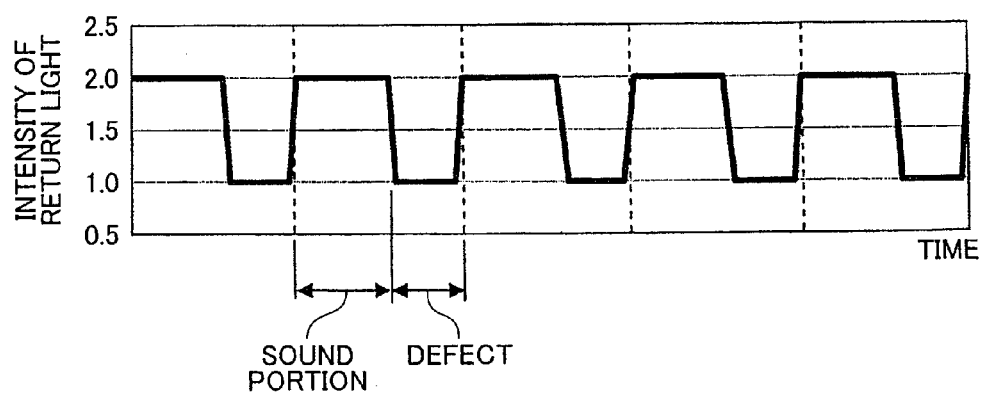
FIG. 10B is a diagram showing the intensity of return light according to the example 2 estimated from the analytical model in time series.
Figure 11A:
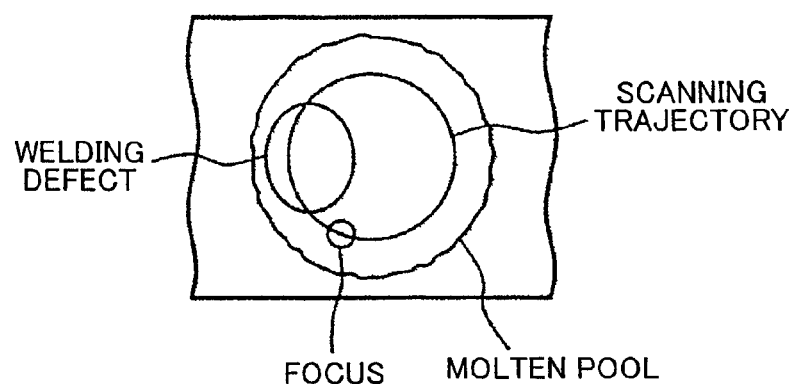
FIG. 11A is an enlarged top view showing the welding portion according to the example 3 based on the analytical model.
Figure 11B:
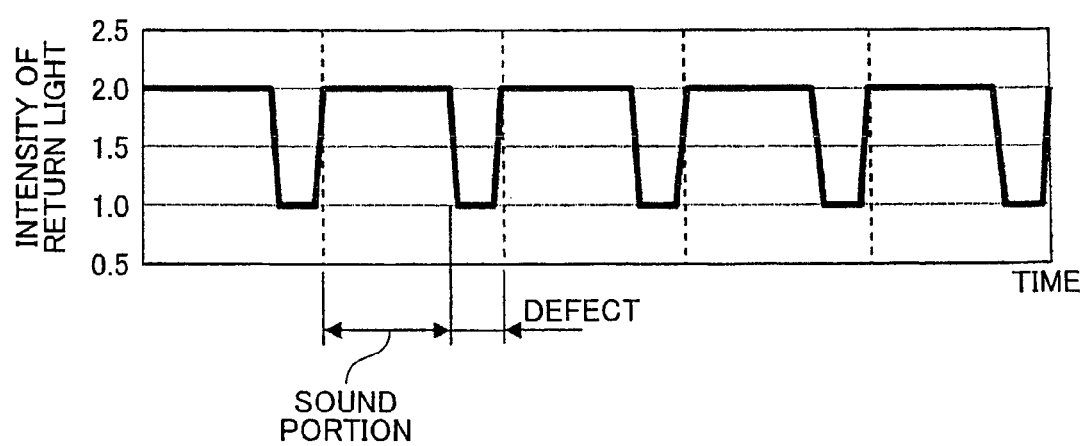
FIG. 11B is a diagram showing the intensity of return light according to the example 3 estimated from the analytical model in time series.
Figure 12A:
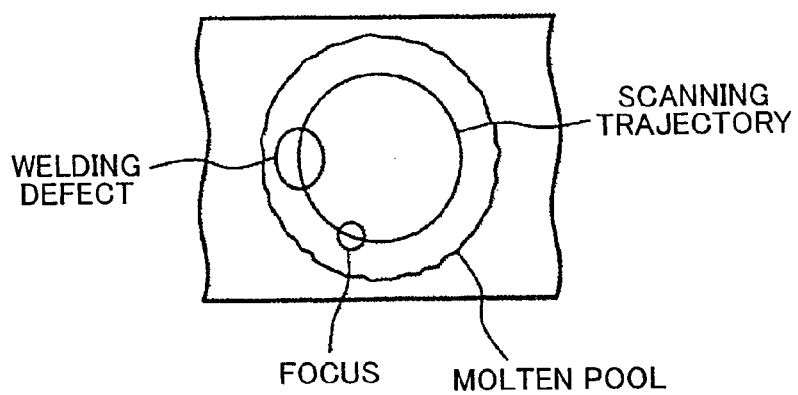
FIG. 12A is an enlarged top view showing the welding portion according to the example 4 based on the analytical model.
Figure 12B:
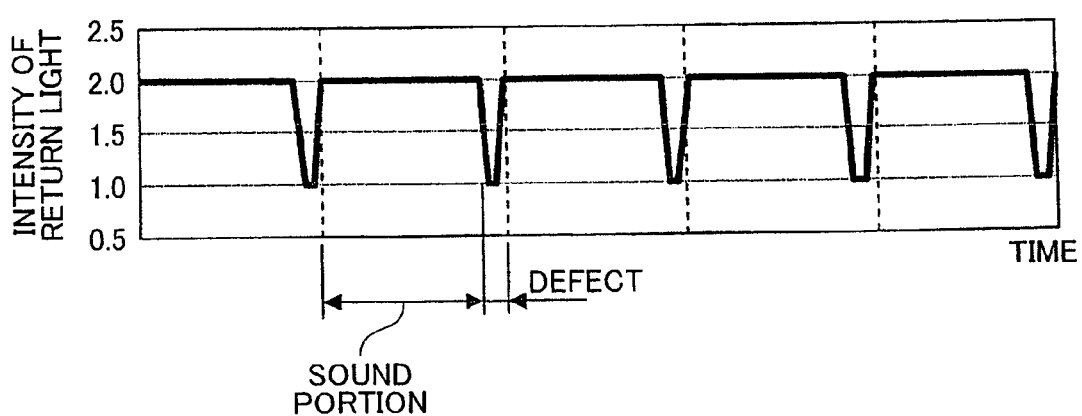
FIG. 12B is a diagram showing the intensity of return light according to the example 4 estimated from the analytical model in time series.

Thus, as shown in FIGS. 9B, 10B, 11B and 12B, it was estimated that a ratio of a time when the inspection laser beam irradiated at a substantially constant speed passes the welding defect with respect to a time when it passes the sound portion of the scanning trajectory was 1.00 in the example shown in FIG. 9B, 0.67 in the example 2 shown in FIG. 10B, 0.33 in the example 3 shown in FIG. 11B and 0.11 in the example 4 shown in FIG. 12B.

<Result of Evaluating a Relationship Between the Intensity of the Return Light and the Size of the Welding Defect in the Welding Portion According to Analytical Model>

Figure 13:
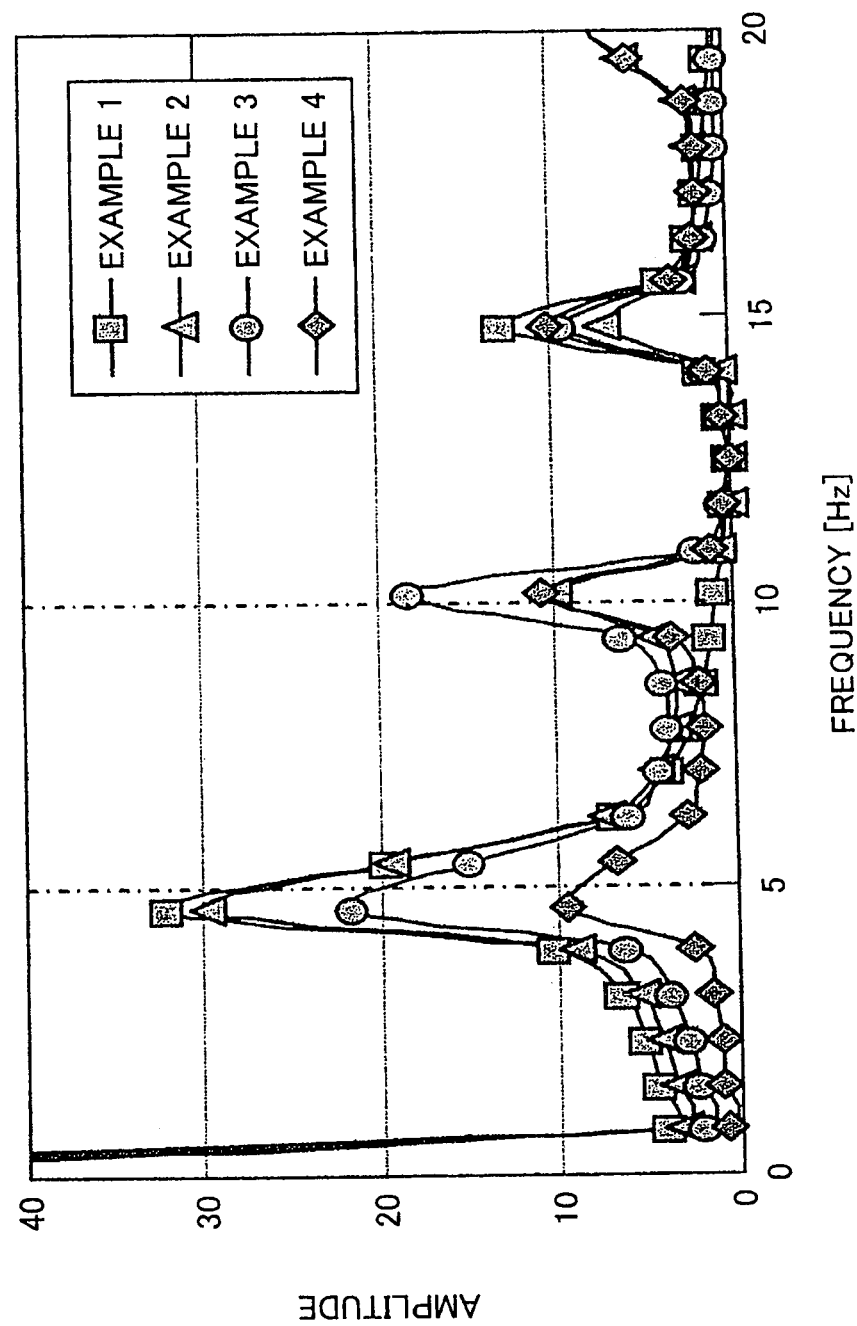
FIG. 13 is a diagram showing a relationship between the frequency of return light and the amplitude according to the examples 1-4 estimated from the analytical model.

FIG. 13 is a diagram showing a relationship between the frequency and the amplitude of the return light in the examples 1 to 4 estimated from the analytical model;

When fast Fourier transform was conducted on the intensities of the return lights in the examples 1 to 4 shown in FIGS. 9B, 10B, 11B, 12B, the amplitude peak in each analytical model of the examples 1 to 4 was confirmed at frequencies of approximately 5 Hz, approximately 10 Hz and approximately 15 Hz, as shown in FIG. 13. In the analytical model of the example 1, no large amplitude peak was confirmed at a frequency of approximately 10 Hz.

Figure 14:
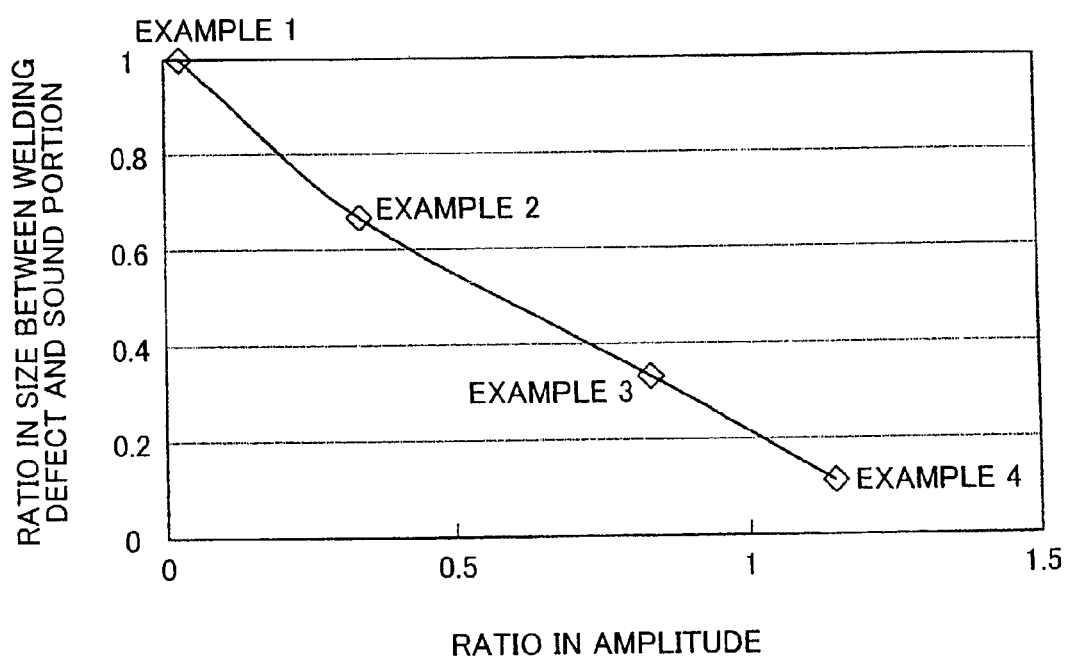
FIG. 14 is a diagram showing a relationship between a ratio of the amplitude under a frequency twice the fundamental frequency with respect to the amplitude under the fundamental frequency according to the examples 1 to 4 based on an analytical model and a ratio of the size of a welding defect with respect to the size of a sound portion of the welding portion.

FIG. 14 is a diagram showing a relationship between the ratio between the amplitude under the fundamental frequencies of the examples 1 to 4 according to the analytical models and the amplitude under another frequency twice the fundamental frequency and the ratio between the size of the sound portion of the welding portion (length passing the sound portion in the scanning trajectory) and the size of the welding defect (length passing the welding defect in the scanning trajectory).

From a relationship between the frequency and the amplitude after fast Fourier transform in the analytical models of the examples 1 to 4, the ratio between the amplitude under approximately 5 Hz (fundamental frequency) in which the amplitude peak was first detected and the amplitude under approximately 10 Hz (frequency that is twice as high as the fundamental frequency) (see FIG. 13) was compared with the ratio between the length passing the sound portion of the scanning trajectory of the inspection laser beam and the length passing the welding defect. As a result, as shown in FIG. 14, it was confirmed that the both had a close correlation. More specifically, it was confirmed that as the ratio between the amplitude under the fundamental frequency and the amplitude under a frequency that is twice as high as the fundamental frequency increased, the ratio between the length passing the sound portion of the scanning trajectory of the inspection laser beam and the length passing the welding defect decreased.

From the analytical result, a fundamental frequency is detected by conducting Fourier transform on the intensity of the return light which is received when the welding laser beam is irradiated along the welding trajectory or the inspection laser beam is irradiated along the scanning trajectory. Then, a ratio of an amplitude under a frequency that is twice as high as the fundamental frequency with respect to an amplitude under the fundamental frequency is calculated. As a result, it has been found that the size of the welding defect which can be formed in the welding portion such as perforated welding in which both the works melted and dropped, one side work depressed welding in which one side work melted and dropped can be inspected precisely.

Although the embodiments of the present invention have been described in detail with reference to the drawings above, the specific structure of the invention is not restricted to these embodiments but any modifications and the like of designs of the present invention shall be included in the present invention as long as they never depart from the gist of the present invention.

The invention claimed is:

1. A welding portion inspection device configured to inspect a welding condition of a welding portion formed when a plurality of works is welded together, the welding portion inspection device comprising:
    an irradiation portion configured to irradiate welding laser beam along a welding trajectory set in works or irradiate inspection laser beam along a scanning trajectory set in a molten pool of the work melted by the welding laser beam so as to weld together the works;
    a light receiving portion configured to receive return light including at least one of reflected light from the molten pool in the work by the welding laser beam or the inspection laser beam irradiated by the irradiation portion, evaporation luminescence which is generated by evaporating of the work, and thermal radiation light radiated from the molten pool in the work; and
    an inspecting portion configured to inspect the welding condition of the welding portion in the work based on an amplitude under a fundamental frequency which is detected by conducting Fourier transform on intensity of the return light received by the light receiving portion and another amplitude under a frequency that is twice as high as the fundamental frequency, wherein
    the irradiation portion irradiates the welding laser beam along an identical welding trajectory several times or irradiates the inspection laser beam along an identical scanning trajectory several times, wherein
    the inspecting portion is configured to analyze a periodical signal obtained by irradiating the welding laser beam along the identical welding trajectory several times or irradiating the inspection laser beam along the identical scanning trajectory several times.

2. The welding portion inspection device according to claim 1, wherein
    the inspecting portion inspects size of the welding defect in the welding portion of the work based on a ratio between the amplitude under the fundamental frequency and the amplitude under the frequency that is twice as high as the fundamental frequency.

3. A welding portion inspection method adapted to inspect a welding condition of a welding portion formed when a plurality of works is welded together, the welding portion inspection method comprising:
    irradiating the welding laser beam along the welding trajectory set in works or irradiating the inspection laser beam along the scanning trajectory set in the molten pool of the work melted by the welding laser beam so as to weld together the works;
    receiving return light including at least one of reflected light from the molten pool in the work by the welding laser beam or the inspection laser beam, evaporation luminescence which is generated by evaporating of the work, and thermal radiation light radiated from the molten pool in the work;
    detecting a fundamental frequency by conducting Fourier transform on intensity of the return light; and
    inspecting the welding condition of the welding portion in the work based on an amplitude under the fundamental frequency and another amplitude under another frequency that is twice as high as the fundamental frequency, wherein
    the irradiating includes irradiating the welding laser beam along an identical welding trajectory several times or irradiating the inspection laser beam along an identical scanning trajectory several times, wherein
    the inspecting includes analyzing a periodical signal obtained by irradiating the welding laser beam along the identical welding trajectory several times or irradiating the inspection laser beam along the identical scanning trajectory several times.

4. The welding portion inspection method according to claim 3, wherein
    as for the inspecting, size of the welding defect in the welding portion of the work is inspected based on a ratio between the amplitude under the fundamental frequency and the amplitude under the frequency that is twice as high as the fundamental frequency.

5. The welding portion inspection device according to claim 1, wherein the welding trajectory of the welding laser beam or the scanning trajectory of the inspection laser beam is in a closed loop shape.

6. The welding portion inspection method according to claim 3, wherein the welding trajectory of the welding laser beam or the scanning trajectory of the inspection laser beam is in a closed loop shape.

* * * * *